(12) United States Patent
Funahashi

(10) Patent No.: US 7,680,678 B2
(45) Date of Patent: Mar. 16, 2010

(54) DIAGNOSTIC SUPPORT SYSTEM AND METHOD USED FOR THE SAME

(75) Inventor: Takeshi Funahashi, Kaisei-machi (JP)

(73) Assignee: FUJIFILM Corporation, Tokyo (JP)

( * ) Notice: Subject to any disclaimer, the term of this patent is extended or adjusted under 35 U.S.C. 154(b) by 1356 days.

(21) Appl. No.: 11/086,326

(22) Filed: Mar. 23, 2005

(65) Prior Publication Data

US 2005/0234321 A1 Oct. 20, 2005

(30) Foreign Application Priority Data

Mar. 26, 2004 (JP) ............... 2004-090870

(51) Int. Cl.
*G06Q 10/00* (2006.01)
*G06Q 50/00* (2006.01)
(52) U.S. Cl. .......................................... 705/2
(58) Field of Classification Search ............... 705/2, 705/3
See application file for complete search history.

(56) References Cited

U.S. PATENT DOCUMENTS

| | | | | |
|---|---|---|---|---|
| 5,828,774 A * | 10/1998 | Wang | ........................ | 382/128 |
| 6,031,516 A * | 2/2000 | Leiper | ........................ | 345/629 |
| 6,240,308 B1 * | 5/2001 | Hardy et al. | ................ | 600/407 |
| 6,364,835 B1 * | 4/2002 | Hossack et al. | ............ | 600/443 |
| 2002/0082868 A1 * | 6/2002 | Pories et al. | ................... | 705/3 |
| 2004/0015079 A1 * | 1/2004 | Berger et al. | ................ | 600/437 |

FOREIGN PATENT DOCUMENTS

| | | | |
|---|---|---|---|
| JP | 63-057030 A | 3/1988 | |
| JP | 08-336517 A | 12/1996 | |
| JP | 11-296153 A | 10/1999 | |
| JP | 2002-224045 A | 8/2002 | |
| JP | 2002-263101 A | 9/2002 | |
| JP | 2003-30202 A | 1/2003 | |
| JP | 2003-175023 A | 6/2003 | |
| JP | 2008-166995 A | 7/2008 | |

OTHER PUBLICATIONS

Partial Translation of Japanese Office Action; dated Apr. 28, 2009.
Japanese Office Action dated Sep. 24, 2009 corresponding to Japanese Application No. 2004-090870.

* cited by examiner

*Primary Examiner*—Gerald J. O'Connor
*Assistant Examiner*—Trang Nguyen
(74) *Attorney, Agent, or Firm*—Sughrue Mion, PLLC

(57) ABSTRACT

A diagnostic support system by which anatomical charts can be referred to easily by a simple operation with no need to store image data representing anatomical charts in each medical facility. This system includes a client terminal for transmitting image data, which represents a medical image obtained by imaging intended for diagnosis, and information on an examination utilizing the medical image to the database server, retransmitting the information on the examination to the database server when requesting anatomical chart data, and displaying an image including the anatomical chart based on the anatomical chart data received from the database server; and a database server for recording the received image data etc. in a first recording medium, and retrieving corresponding anatomical chart data from a second recording medium, in which plural kinds of anatomical chart data are recorded, to transmit the retrieved anatomical chart data to the client terminal.

20 Claims, 8 Drawing Sheets

FIG.7

| IMAGING MENU | ANATOMICAL CHART FILENAME | ALPHA CHANNEL INFORMATION |
|---|---|---|
| CEPHALIC PART FRONT | AC001 | 0.4 |
| CEPHALIC PART SIDE | AC002 | 0.4 |
| CERVICAL PART FRONT | AC003 | 0.2 |
| CERVICAL PART SIDE | AC004 | 0.2 |
| THORACIC PART FRONT | AC005 | 0.4 |
| THORACIC PART SIDE | AC006 | 0.4 |
| BREAST | AC007 | 0.2 |
| ABDOMINAL PART FRONT | AC008 | 0.3 |
| ABDOMINAL PART SIDE | AC009 | 0.3 |
| PELVIS | AC010 | 0.4 |
| UPPER LIMB | AC011 | 0.1 |
| LOWER LIMB | AC012 | 0.1 |
| ⋮ | ⋮ | ⋮ |

DIAGNOSTIC SUPPORT SYSTEM AND METHOD USED FOR THE SAME

BACKGROUND OF THE INVENTION

Field of the Invention

The present invention relates to a diagnostic support system of providing information required for diagnosis, from a data center for centrally storing medical data obtained in plural medical facilities, to the respective medical facilities. Furthermore, the present invention relates to a diagnostic support method used in such a diagnostic support system.

Description of a Related Art

Conventionally, in medical facilities such as clinics of general practitioners and hospitals, medical images have been taken using medical image taking apparatuses utilizing radiation (X-ray, α-ray, β-ray, γ-ray, electron beam, ultraviolet light, etc.), ultrasonic wave, MR (magnetic resonance), or the like. Such medical images are required to be stored in order to know the changes in medical conditions of patients, and required to be stored in a predetermined period by law. Accordingly, in the medical facilities, it is necessary to store a vast amount of medical images. Conventionally, films on which medical images are taken, or the like have been stored, and thereby, securing of storage space, management work, and retrieval work of medical images have imposed heavy burdens on the medical facilities.

In recent years, the digitization of medical image taking apparatuses has been proceeding, and the storage space can be reduced, and the management work and the retrieval work can be saved by recording medical images as image data in optical disks, magnetic disks, or the like. However, since one sheet of medical image is represented by a vast amount of image data, even if they are recorded in optical disks, a considerable number of optical disks are required to store medical data in a predetermined period.

Accordingly, a medical image central management system by which image data obtained in plural medical facilities are centrally stored in a database server provided in a data center apart from the medical facilities, and thereby, the necessity for the respective medical facilities to independently store recording media in which medical data have been recorded is eliminated and the space or costs for securing the space can be reduced is realized.

On the other hand, in order to use as an object of comparison when a taken medical image is unclear, or when explaining a taken radiation image to a patient, there is a demand to refer to an anatomical chart depicted as an illustration. In order to refer to anatomical charts easily by a simple operation, a system of referring to anatomical charts recorded as digital signals is desired.

As a related technology, JP-A-2002-263101 discloses an ultrasonic diagnostic apparatus capable of displaying an ultrasonic image with a reference image showing the interior of a living body. In this ultrasonic diagnostic apparatus, an appropriate anatomical chart image can be automatically selected from an anatomical chart DB (database) based on the probe coordinate position, body proportion information, and other information. However, because image data representing all anatomical charts is vast in amount, it is not efficient that the ultrasonic diagnostic apparatus installed in each medical facility retains image data representing all anatomical charts.

Further, in JP-A-2002-263101, there described that the anatomical chart DB may be formed substantially by an external storage device such as a CD-ROM, however, a considerable number of CD-ROMs are required to store image data representing all anatomical charts.

SUMMARY OF THE INVENTION

In view of the above described points, an object of the present invention is to provide a diagnostic support system and method by which anatomical charts can be referred to easily by a simple operation with no need to store image data representing anatomical charts in each medical facility.

In order to solve the above described problems, a diagnostic support system according to an aspect of the present invention is a diagnostic support system formed by connecting a client terminal provided in a medical facility and a database server provided in a data center via a network, the system comprising: a client terminal for transmitting image data which represents a medical image obtained by imaging intended for diagnosis, and information on an examination utilizing the medical image to the database server, retransmitting the information on the examination utilizing the medical image to the database server when requesting anatomical chart data representing a desired anatomical chart, and displaying an image including the anatomical chart based on the anatomical chart data received from the database server; and a database server for recording the image data and the information on the examination, which are received from the client terminal, in a first recording medium, and retrieving corresponding anatomical chart data from a second recording medium, in which plural kinds of anatomical chart data are recorded, based on the received information on the examination to transmit the retrieved anatomical chart data to the client terminal when anatomical chart data is requested.

Further, a diagnostic support method according to an aspect of the present invention is a diagnostic support method to be used in a diagnostic support system formed by connecting a client terminal provided in a medical facility and a database server provided in a data center via a network, the method comprising the steps of: (a) transmitting image data, which represents a medical image obtained by imaging intended for diagnosis, and information on an examination utilizing the medical image from the client terminal to the database server; (b) recording the received image data and information on the examination in a first recording medium in the database server; c) retransmitting the information on the examination utilizing the medical image from the client terminal to the database server when requesting anatomical chart data representing a desired anatomical chart; (d) retrieving corresponding anatomical chart data from a second recording medium, in which plural kinds of anatomical chart data are recorded, based on the received information on the examination in the database server when anatomical chart data is requested; (e) transmitting the retrieved anatomical chart data from the database server to the client terminal; and (f) displaying an image including the anatomical chart in the client terminal based on the anatomical chart data received from the database server.

According to the present invention, the information on the examination utilizing the medical image is retransmitted from the client terminal to the database server when requesting the anatomical chart data representing a desired anatomical chart, and the corresponding anatomical chart data is retrieved from the second recording medium, in which plural kinds of anatomical chart data are stored, based on the received information on the examination in the database server, and thereby, a diagnostic support system and method by which the anatomical chart can be referred to easily by a simple operation with no need to store the image data representing anatomical charts in each medical facility can be provided.

BRIEF DESCRIPTION OF THE DRAWINGS

FIG. 7 shows an example of an anatomical chart retrieval table recorded in an anatomical chart database.

DESCRIPTION OF THE PREFERRED EMBODIMENTS

Figure 1:
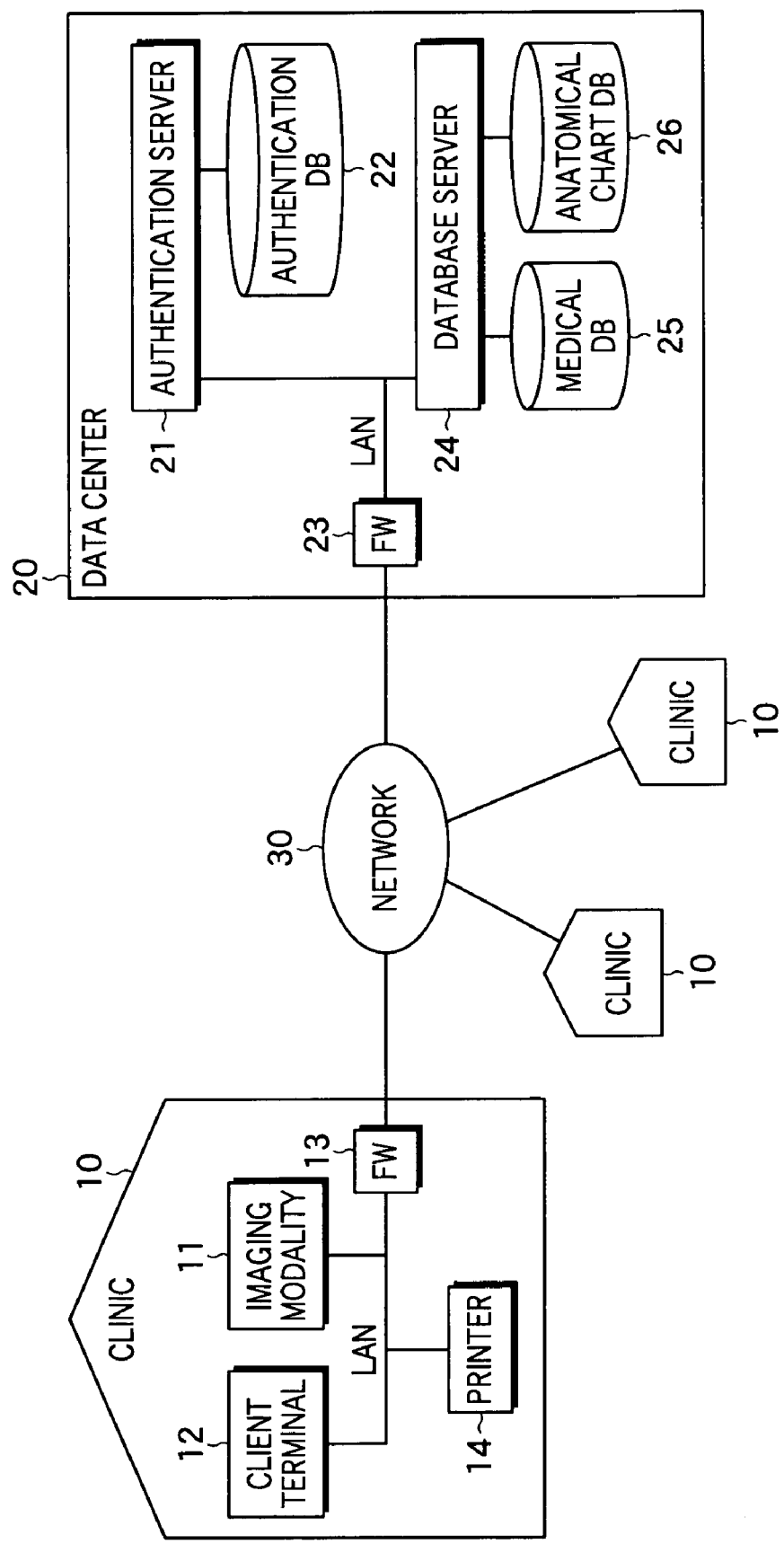
FIG. 1 is a schematic diagram showing a configuration of a diagnostic support system according to one embodiment of the present invention.

Hereinafter, the best mode of the present invention will be described in detail by referring to the drawings. The same reference numerals are assigned to the same component elements and the description thereof will be omitted.

FIG. 1 is a schematic diagram showing a configuration of a diagnostic support system according to one embodiment of the present invention. As shown in FIG. 1, this diagnostic support system includes plural clinics 10 as examples of medical facilities which are connected to a data center 20 via a network 30 such as a dedicated line, a public switched telephone network (PSTN), the Internet, or the like.

In the respective clinics 10, imaging modalities 11 such as radiation image taking apparatuses or ultrasonic diagnostic apparatuses, client terminals 12 to which medical data such as image data representing medical images is inputted from the imaging modalities 11 for transferring the data to the data center 20, firewalls (FW) 13 for preventing unauthorized access, printers 14 for printing out medical images on films or the like, etc. are connected via local area networks (LANs) to one another.

In the clinic 10, patient attribution information and examination attribution information are inputted by an operator or from another terminal, and imaging of an examinee using the imaging modality 11 is performed according to an instruction by the operator based on such information. Here, the patient attribution information corresponds to information representing name of patient, ID number, date of birth, age, sex, etc. Further, the examination attribution information corresponds to information representing date of examination, date of consultation, imaging menu, part to be examined, image feature, etc. The imaging menu includes parts to be imaged as targets of imaging such as cephalic part, cervical part, and abdominal part, and imaging method as imaging directions toward a patient such as front and side. The part to be examined is thoracic part, thoracoabdominal part, four limbs, lumber spine, etc. as targets of examination.

In the embodiment, the client terminal 12 transmits an information request signal based on the imaging menu, the part to be examined, the image feature, etc. included in the examination attribution information, and downloads anatomical chart data used for diagnosis from the data center 20, and thereby, space required for storing anatomical chart data can be reduced in the clinic 10.

In the data center 20, an authentication server 21 for authenticating access from client terminals 12, an authentication database (DB) 22 for recording user information required for authentication, a firewall (FW) 23 for preventing unauthorized access, a database server 24 for managing the medical data transmitted from the client terminals 12, a recording medium such as a hard disk in which a medical database (DB) 25 for accumulating the medical data is recorded, and a recording medium such as a hard disk in which an anatomical chart database (DB) 26 for storing anatomical chart data and an anatomical chart retrieval table are recorded are provided. In the embodiment, the authentication server 21 is provided within the data center 20, however, the authentication server 21 may be provided outside of the data center 20.

In the embodiment, the database server 24 retrieves anatomical chart data used for diagnosis from the anatomical chart database 26 based on the imaging menu, part to be examined, or image feature included in the information request signal transmitted from the client terminal 12 and transmits the data to the client terminal 12, and thereby, space required for storing anatomical chart data is reduced in the clinic 10.

Anatomical chart filenames are given to data files in anatomical chart data stored in the anatomical chart database 26. Further, in the anatomical chart retrieval table, the imaging menu, the part to be examined, or the image feature, and an anatomical chart filename, and alpha channel information representing degree of transparency when an anatomical chart is displayed while being superimposed on a medical image are associated.

Figure 2:
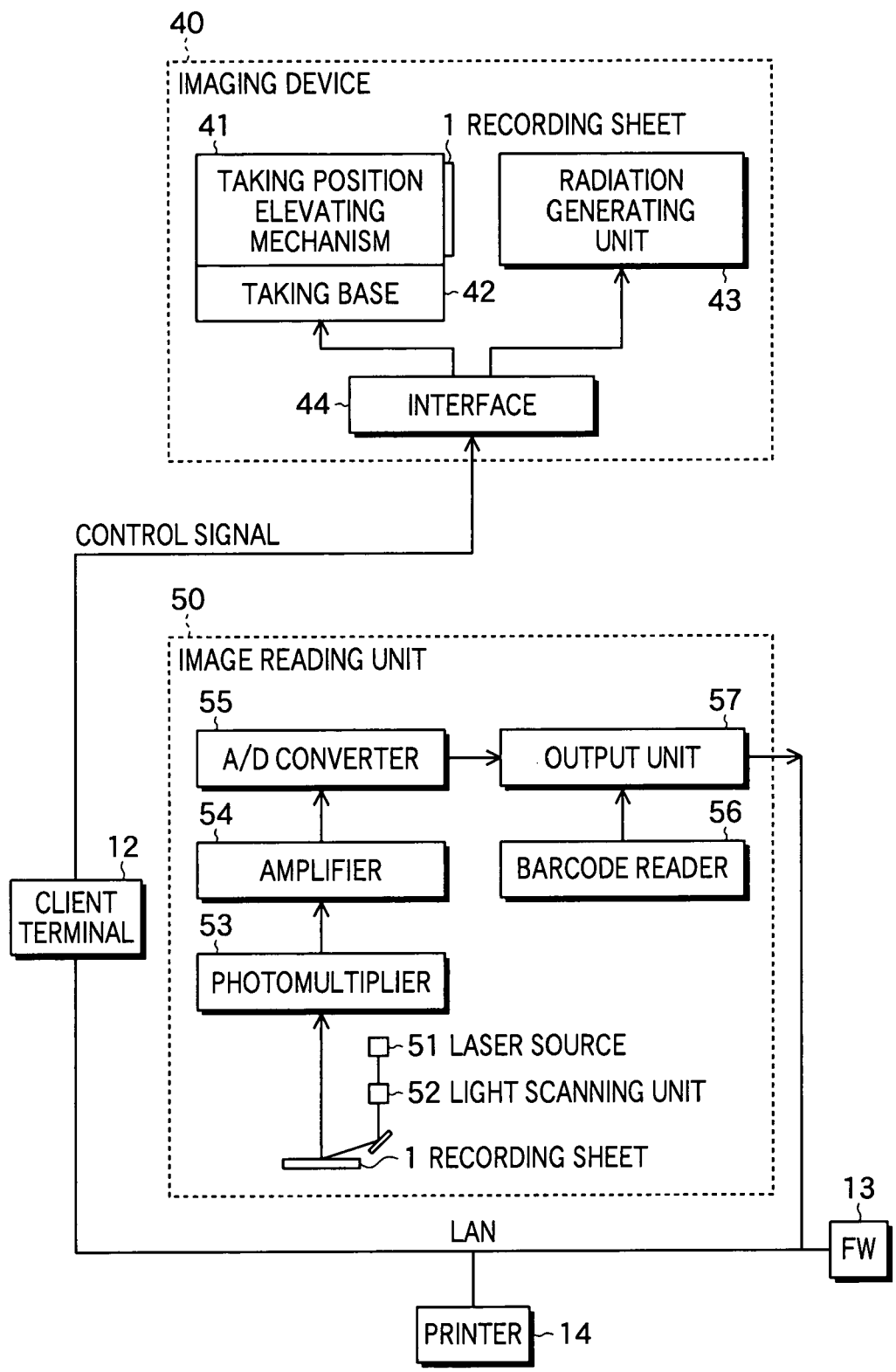
FIG. 2 is a block diagram showing the configuration including a radiation image taking apparatus used in the one embodiment of the present invention.

Next, the case of using a radiation image taking apparatus as the imaging modality 11 to generate image data will be described by referring to FIG. 2. As shown in FIG. 2, the radiation image taking apparatus includes an imaging device 40 for recording a radiation image on a recording sheet 1 by performing imaging by applying radiation to an examinee, and an image reading device 50 for photoelectrically reading information such as the radiation image recorded on the recording sheet 1, and generating image data and image-associated information associated with the radiation image. The recording sheet 1 is coated with a photostimulable phosphor material, and information on a subject is recorded thereon by applying radiation thereto. The photostimulable phosphor material (accumulative phosphor) is a material in which, when applied with radiation, part of radiation energy is accumulated, and then, when applied with excitation light such as visible light, photostimulably emits light according to the accumulated energy.

The imaging device 40 includes a taking position elevating mechanism 41 for elevating the taking position in the examinee by finely adjusting the position of the recording sheet 1 set in a predetermined position to move upward or downward, a taking base 42 for positioning the feet of the examinee, a radiation generating unit 43 for applying radiation to the examinee, and an interface 44 to which control signals are inputted from the client terminal 12.

The image reading device 50 scans the surface of the recording sheet 1 set in a predetermined position with a light beam outputted from a laser source 51 and passing through the light scanning unit 52. By the scanning, the light beam is applied to the recording sheet 1, and photostimulably emitted light is generated in an amount of light depending on the radiation image information that has been accumulatively recorded from the location applied with the light beam. The photostimulably emitted light is photoelectrically detected by a photomultiplier 53, outputted as analog signals, amplified by an amplifier 54, and digitized by an A/D converter 55. Further, a barcode attached to a cassette in which the recording sheet 1 is stored is read by a barcode reader 56, and the read barcode information is used as image-associated information corresponding to patient attribution information and examination attribution information. Thus generated image data and image-associated information are transmitted from an output unit 57 via a LAN to the client terminal 12.

The client terminal 12 controls the imaging device 40 in response to the instruction by the operator, and the image data and the image-associated information are inputted from the image reading device 50 and temporarily stored there. In the client terminal 12, image processing can be performed on the image data, or images for diagnosis can be displayed based on the image data and the image-associated information on a display or the like. Note that, because a vast amount of image data are daily accumulated, they are stored not for a long period in the clinic, but transferred to the data center apart from the clinic and stored there. Thereby, in the clinic, space for storing recording media in which medical data have been recorded, or costs for securing the space can be reduced.

Figure 3:
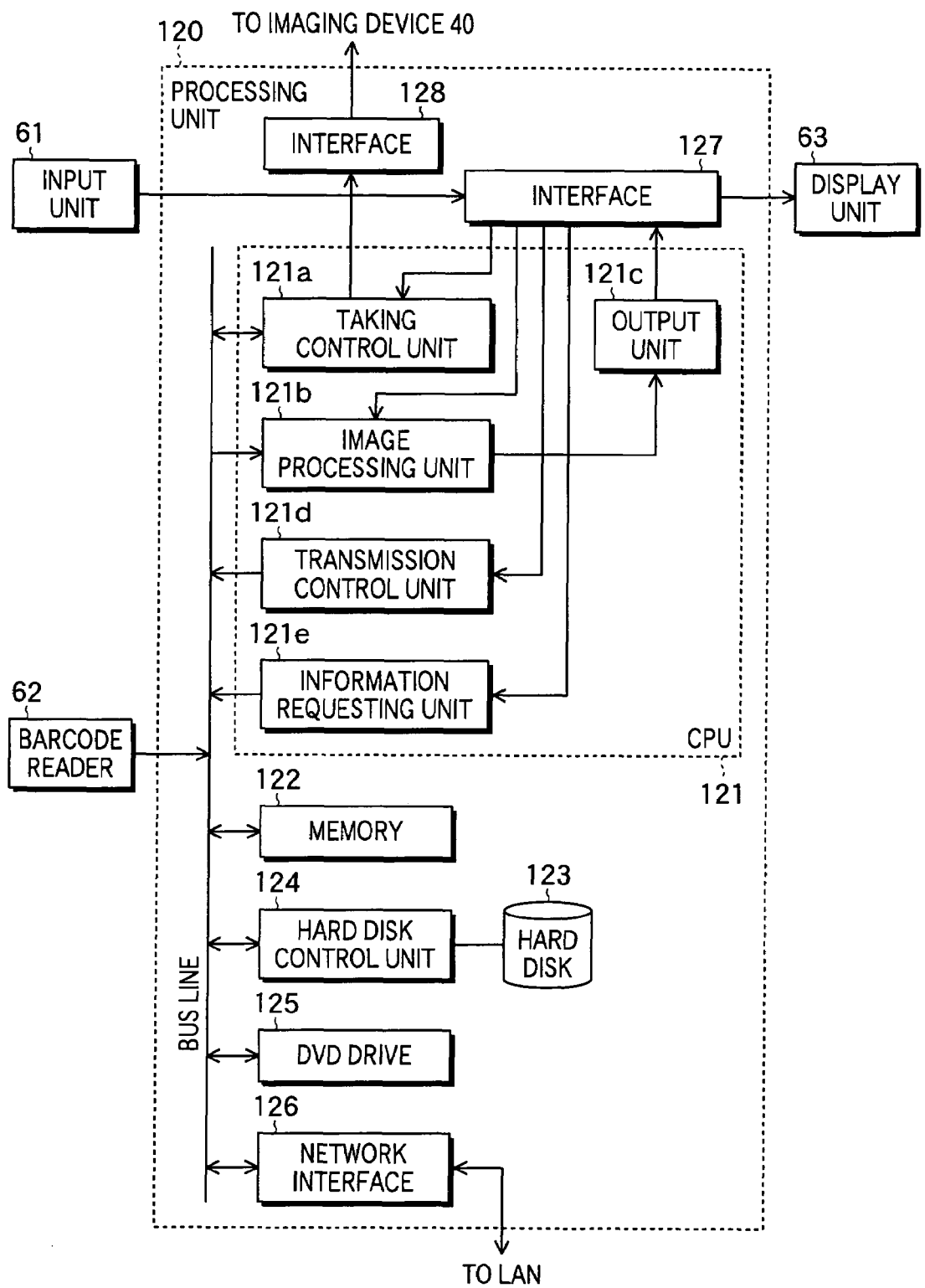
FIG. 3 is a block diagram showing the constitution of a client terminal.

FIG. 3 is a block diagram showing the constitution of the client terminal. The client terminal 12 includes an input unit 61 used for inputting the patient attribution information, the examination attribution information and various kinds of instructions, a barcode reader 62 for reading a barcode attached to a cassette in which the recording sheet 1 is stored, a display unit 63 for displaying images for diagnosis or the like, and a processing unit 120. The medical images read by the image reading device 50 (FIG. 2) are correlated with the patient attribution information and the examination attribution information, which are stored in the client terminal 12, based on the barcode information read from the cassette using the barcode reader 62 in advance before taking.

The processing unit 120 includes a central processing unit (hereinafter, referred to as "CPU") 121, a memory 122 for temporarily storing inputted image data, image-associated information and anatomical chart data, a hard disk 123 as a recording medium, a hard disk control unit 124, a DVD drive 125 for performing writing and reading on a DVD (digital versatile disk), and a network interface 126 for connection to a LAN. These parts 121 to 126 are connected to one another via a bus line.

Furthermore, the processing unit 120 includes interfaces 127 and 128. The CPU 121 is connected via the interface 127 to the input unit 61 such as a keyboard or mouse and the display unit 63 such as a CRT display, and connected via the interface 128 to the imaging device 40.

The memory 122 temporarily stores the inputted patient attribution information and examination attribution information, the image data and the image-associated information which are received from the image modality 11, and the anatomical chart data received from the data center 20. In the hard disk 123, software (program) for allowing the CPU 121 to perform operation is recorded. As the recording medium for recording the program, not only the built-in hard disk 123, but also an external hard disk, a flexible disk, an MO, an MT, a RAM, a CD-ROM, a DVD-ROM, or the like may be used.

Next, function blocks 121*a* to 121*e* formed by the CPU 121 and software (program) will be described.

The taking control unit 121*a* controls, via the interface 128, the imaging device 40 to start an examination based on the patient attribution information and the examination attribution information which are stored in the memory 122.

The image processing unit 121*b* performs necessary image processing on the image data received from the image reading device 50, and generates display data for display on the display unit 63. Further, the image processing unit 121*b* generates display data for display on the display unit 63 based on the anatomical chart data received from the data center 20. The display data is supplied from the output unit 121*c* via the interface 127 to the display unit 63, images are displayed on the display unit 63, and the images are confirmed by an operator. Further, the image data subjected to the necessary image processing is stored in the memory 122, and recorded in the hard disk 123 under the control of the hard disk control unit 124 according to the set conditions.

When desired image data is thus obtained, in order to store the medical data such as image data in the data center 20, the transmission control unit 121*d* starts to access the data center 20 according to the instructions using the input unit 61 by the operator or set conditions. In the data center 20, in order to prevent the leaks of personal information, the falsification of medical image data, or the like, an authentication is requested to access to the database server 24 (FIG. 1), and access to the database server 24 is inhibited until it is allowed by the authentication.

When the transmission control unit 121*d* makes inquiries about access right to the authentication server 21 (FIG. 1) of the data center 20 and the access right is authenticated in the authentication server 21, the transmission control unit 121*d* transmits the medical data, which is stored in storage means such as the memory 122 or hard disk 123, to the database server 24 and allows the server to record the data.

The information requesting unit 121*e* starts to access to the data center 20 in response to the instruction for downloading the anatomical chart inputted by the operator using the input unit 61. In the same operation as described in the transmission control unit 121*d*, when the access right is authenticated in the authentication server 21, the information requesting unit 121*e* transmits an information request signal to the database server 24 so that the database server 24 may transmit anatomical chart data. Here, the information request signal includes image-associated information such as patient attribution information or examination attribution information, and information for identifying the transmission source of the information request signal such as medical facility serial number.

By the way, in the embodiment, the taking control unit 121*a*, the image processing unit 121*b*, the output unit 121*c*, the transmission control unit 121*d*, and the information requesting unit 121*e* are formed by a CPU and software, however, they may be formed by digital circuits or analog circuits.

Figure 4:
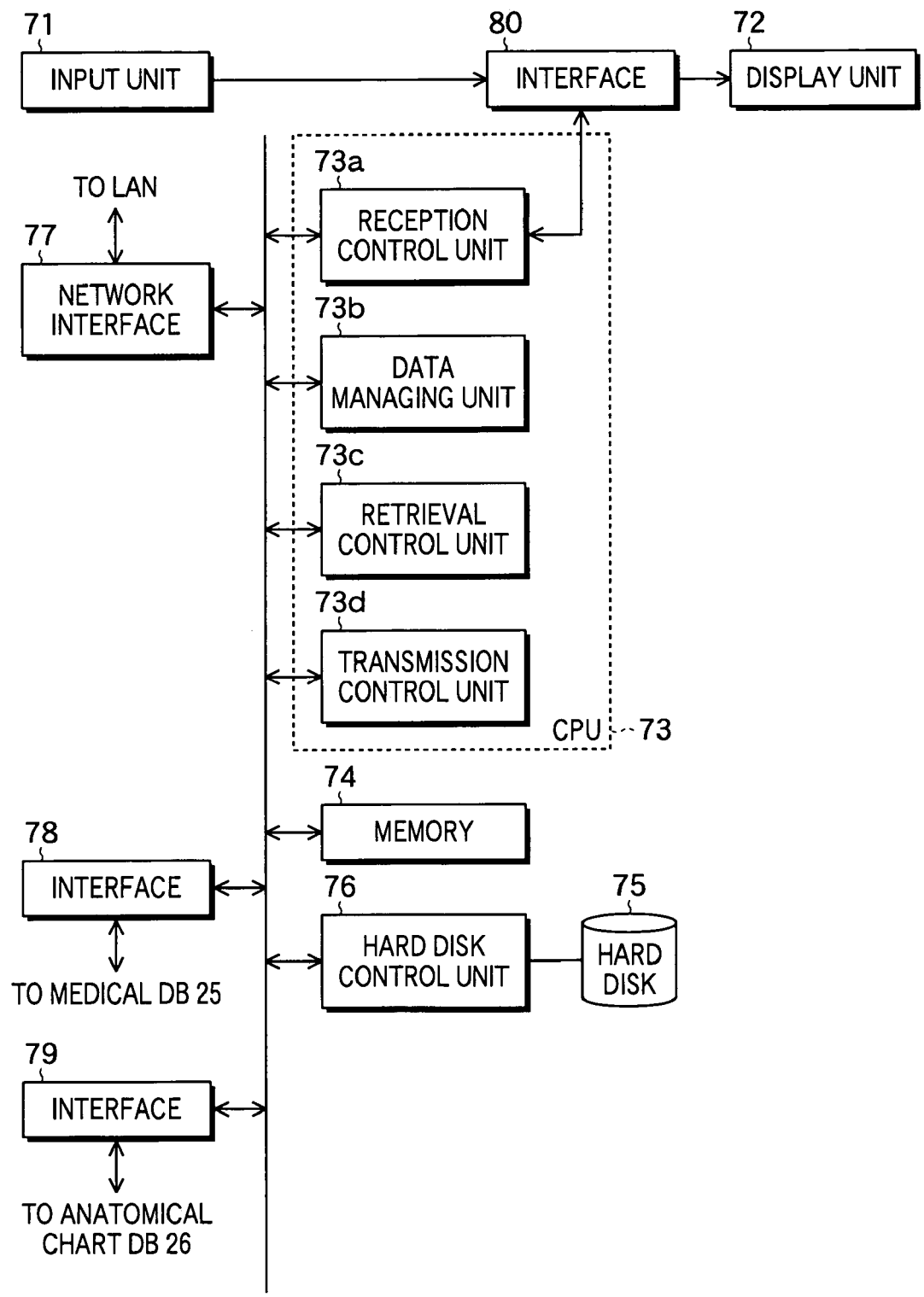
FIG. 4 is a block diagram showing the constitution of a database server.

FIG. 4 is a block diagram showing the constitution of the database server. The database server 24 includes an input unit 71 used for inputting various kinds of instructions, a display unit 72 for display for operation, a central processing unit (hereinafter, referred to as "CPU") 73 to which the input unit 71 and the display unit 72 are connected via an interface 80, a memory 74 for temporarily storing the medical data and the information request signal which are received from the client terminal 12 (FIG. 1), a hard disk 75, a hard disk control unit 76 for controlling the hard disk 75, a network interface 77 for connection to a LAN, an interface 78 for controlling the medical database 25, and an interface 79 for controlling the anatomical chart database 26. These parts 71 to 79 are connected to one another via a bus line.

The memory 74 temporarily stores the medical data and the information request signal which are received from the client terminal 12 (FIG. 1). In the hard disk 75, software (program) for allowing the CPU 73 to perform operation is recorded. As the recording medium for recording the program, not only the built-in hard disk 75, but also an external hard disk, a flexible disk, an MO, an MT, a RAM, a CD-ROM, a DVD-ROM, or the like may be used.

Next, function blocks 73a to 73d formed by the CPU 73 and software (program) will be described.

The reception control unit 73a receives the medical data transmitted from the client terminal (FIG. 1), and the information request signal including the image-associated information. The data managing unit 73b manages the medical data received by the reception control unit 73a by recording the medical data in the recording medium of the medical database 25, and manages the anatomical chart data by recording the anatomical chart data in the anatomical chart database 26.

The retrieval control unit 73c reads out an anatomical chart filename from the anatomical chart retrieval table, which is recorded in the anatomical chart database 26, using the imaging menu, the part to be examined, the image feature, or the like of the examination attribution information which is contained in the information request signal received by the reception control unit 73a, as a retrieval keyword. Further, the retrieval control unit 73c retrieves anatomical chart data used for diagnosis recorded in the anatomical chart database 26, based on the read anatomical chart filename.

The transmission control unit 73d transmits the retrieved anatomical chart data used for diagnosis to the client terminal 12 (FIG. 1) of the transmission source based on the information for identifying the transmission source of the information request signal such as a medical facility serial number which is contained in the information request signal received by the reception control unit 73a.

In the embodiment, the client terminal 12 (FIG. 1) transmits the examination attribution information on diagnosis and examination of a patient to the database server 24, and the database server 24 which receives the examination attribution information transmits the anatomical chart data used for diagnosis to the client terminal 12 (FIG. 1). Thereby, the anatomical chart can be browsed by the simple operation of the client terminal 12 (FIG. 1) while suppressing the space required for storing anatomical chart data in the clinic 10.

By the way, the reception control unit 73a, the data managing unit 73b, the retrieval control unit 73c, and the transmission control unit 73d are formed by the CPU and software (program), however, they may be formed by digital circuits or analog circuits.

Figure 5:
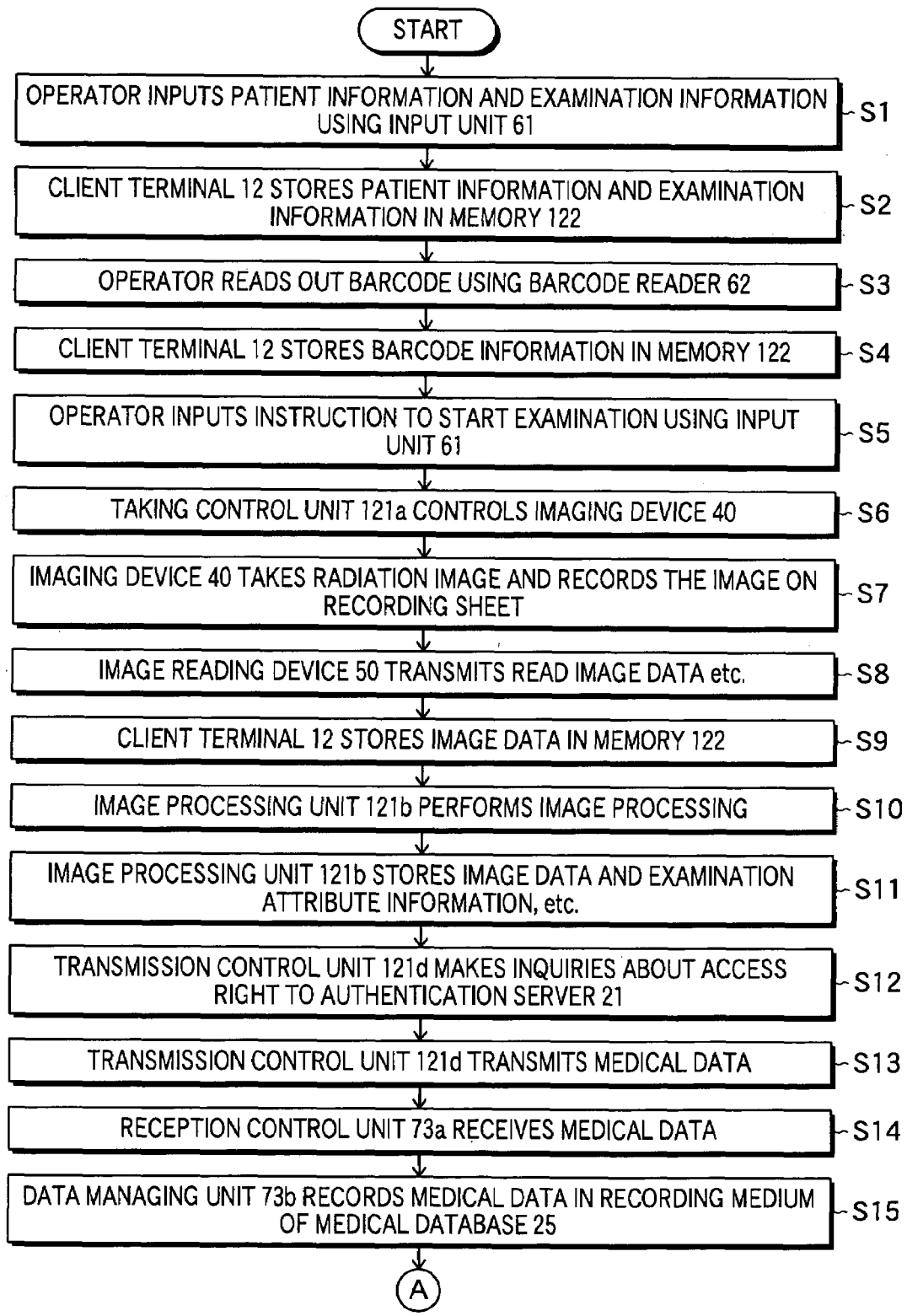
FIG. 5 is a flowchart showing the operation of the diagnostic support system in the embodiment.
Figure 6:
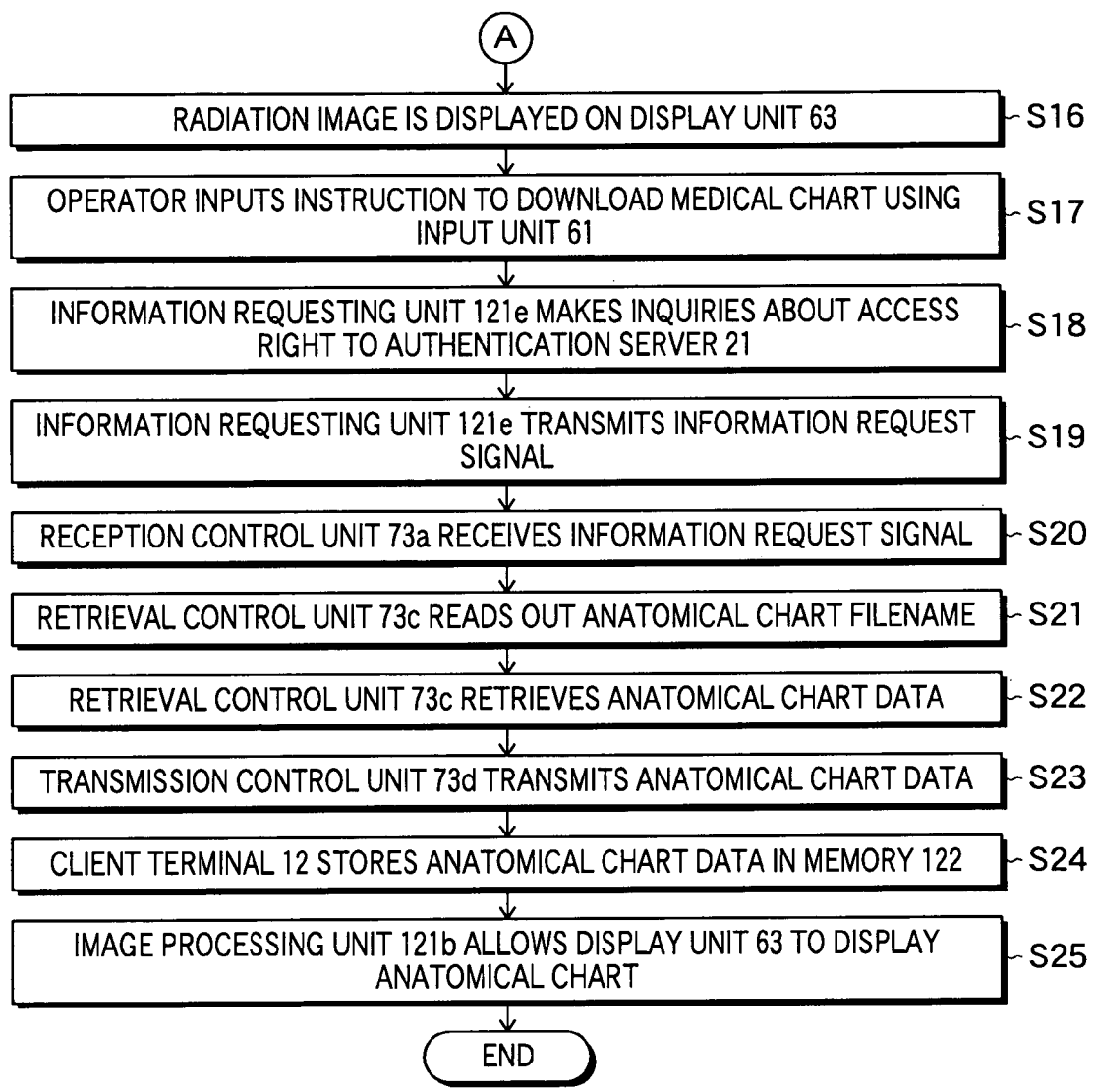
FIG. 6 is a flowchart showing the operation of the diagnostic support system in the embodiment.

Next, the operation of the diagnostic support system according to the embodiment will be described by referring to FIGS. 1 to 6. FIGS. 5 and 6 are flowcharts showing the operation of the diagnostic support system in the embodiment.

At step S1, the operator inputs the patient attribution information and the examination attribution information using the input unit 61 of the client terminal 12. By the way, these information may be inputted from another terminal such as a receipt computer. Then, at step S2, the client terminal 12 stores the patient attribution information and the examination attribution information, which are inputted via the interface 127 using the input unit 61, in the memory 122.

At step S3, the operator reads out the barcode attached to the cassette in which the recording sheet is stored, using the barcode reader 62. At step S4, the client terminal 12 stores the barcode information generated by reading out the barcode, in association with the patient attribution information and the examination attribution information in the memory 122.

At step S5, the operator inputs an instruction to start an examination using the input unit 61. At step S6, the taking control unit 121a controls the imaging device 40 based on the patient attribution information and the examination attribution information in response to the instruction to start the examination. At step S7, the imaging device 40 takes a radiation image by applying radiation to an examinee under the control of the taking control unit 121a, and records the radiation image onto the recording sheet.

At step S8, the image reading device 50 generates image data by reading the radiation image recorded on the recording sheet 1, and transmits the generated image data with the barcode information to the client terminal 12.

At step S9, the client terminal 12 stores the image data and the barcode information which are received from the image reading device 50, in the memory 122. Here, the client terminal 12 matches the barcode information received from the medical image reading device 50 with the barcode information generated by the barcode reader 62, and thereby, associates the image data with the patient attribution information and the examination attribution information.

At step S10, the image processing unit 121b performs image processing on the image data stored in the memory 122. At step S11, the image processing unit 121b stores the image data representing the medical images, and the patient attribution information and the examination attribution information which are associated with the medical images, in storage means such as the hard disk 123.

At step S12, the transmission control unit 121d makes inquiries about access right to the authentication server 21 of the data center 20. When the access right is authenticated by the authentication server 21, at step S13, the transmission control unit 121d transmits the stored medical data such as image data from the client terminal 12 to the database server 24 of the data center 20.

At step S14, the reception control unit 73a of the database server 24 receives the medical data. At step S15, the data managing unit 73b records the medical data received by the reception control unit 73a, in the recording medium of the medical data base 25. Thereby, the medical image data is stored in the data center 20.

Referring to FIG. 6, at step S16, radiation images are displayed on the display unit 63 of the client terminal 12 based on the image data subjected to image processing at step S10.

Then, at step S17, a doctor as the operator performs consultation while interpreting the radiation images being displayed on the display unit 63, and inputs an instruction to download an anatomical chart using the input unit 61. At step S18, the information requesting unit 121e makes inquiries about access right to the authentication server 21 of the data center 20 in response to the instruction to download the anatomical chart.

When the access right is authenticated by the authentication server 21, at step S19, the information requesting unit 121e transmits an information request signal from the client terminal 12 to the database server 24 of the data center 20 so that the data center 20 may transmit anatomical chart data. The information request signal contains information for identifying the transmission source such as the medical facility serial number with the imaging menu, the part to be examined, the image feature, etc.

Then, at step S20, the reception control unit 73a of the database server 24 receives the information request signal. At step S21, the retrieval control unit 73c reads out the corresponding anatomical chart filename and alpha channel information from the anatomical chart retrieval table recorded in the anatomical chart database 26, using the imaging menu, the part to be examined, the image feature, or the like of the examination attribution information, which are contained in the information request signal received by the reception control unit 73a, as a retrieval keyword. At step S22, the retrieval control unit 73c retrieves anatomical chart data used for diagnosis from the anatomical chart database 26 based on the read anatomical chart filename.

FIG. 7 shows an example of the anatomical chart retrieval table recorded in the anatomical chart database. As shown in FIG. 7, in the anatomical chart retrieval table, the imaging menu, the anatomical chart filenames of data files in which anatomical chart data are stored, and the alpha channel information are stored in association with one another. For example, imaging menu "cephalic part front", anatomical chart filename "AC001", and alpha channel information "0.4" are associated. Further, imaging menu "cephalic part side", anatomical chart filename "AC002", and alpha channel information "0.4" are associated. Similarly, imaging menu "thoracic part front", anatomical chart filename "AC005", and alpha channel information "0.4" are associated Therefore, when the reception control unit 73a receives an information request signal containing "thoracic part front" as an imaging menu item, the retrieval control unit 73c reads out "AC005" as the corresponding anatomical chart filename from the anatomical chart retrieval table based on the retrieval keyword of "thoracic part front", and reads out "0.4" as the corresponding alpha channel information. Further, the retrieval control unit 73c retrieves anatomical chart data of anatomical chart filename "AC005" from the anatomical chart database 26 based on the read anatomical chart filename "AC005".

Similarly, in the anatomical chart retrieval table, the parts to be examined, the image features, or the like may be associated with the anatomical chart filenames, and the anatomical chart filename may be read out based on the part to be examined, the image feature, or the like contained in the examination attribution information for retrieval of anatomical chart data.

Referring to FIG. 6 again, at step S23, the transmission control unit 73d returns the anatomical chart data and the alpha channel information, which are used for diagnosis, to the client terminal 12 of transmission source based on the information for identifying the transmission source of the information request signal such as a medical facility serial number contained in the information request signal received by the reception control unit 73a.

At step S24, the client terminal 12 stores the received anatomical chart data and alpha channel information in the memory 122. At step S25, the image processing unit 121b allows the display unit 63 to display an anatomical chart based on the anatomical chart data stored in the memory 122. The image processing unit 121b displays the anatomical chart and the radiation image side by side, or displays the anatomical chart superimposed on the radiation image, based on the display form command inputted by the operator using the input unit 61.

Figure 8:
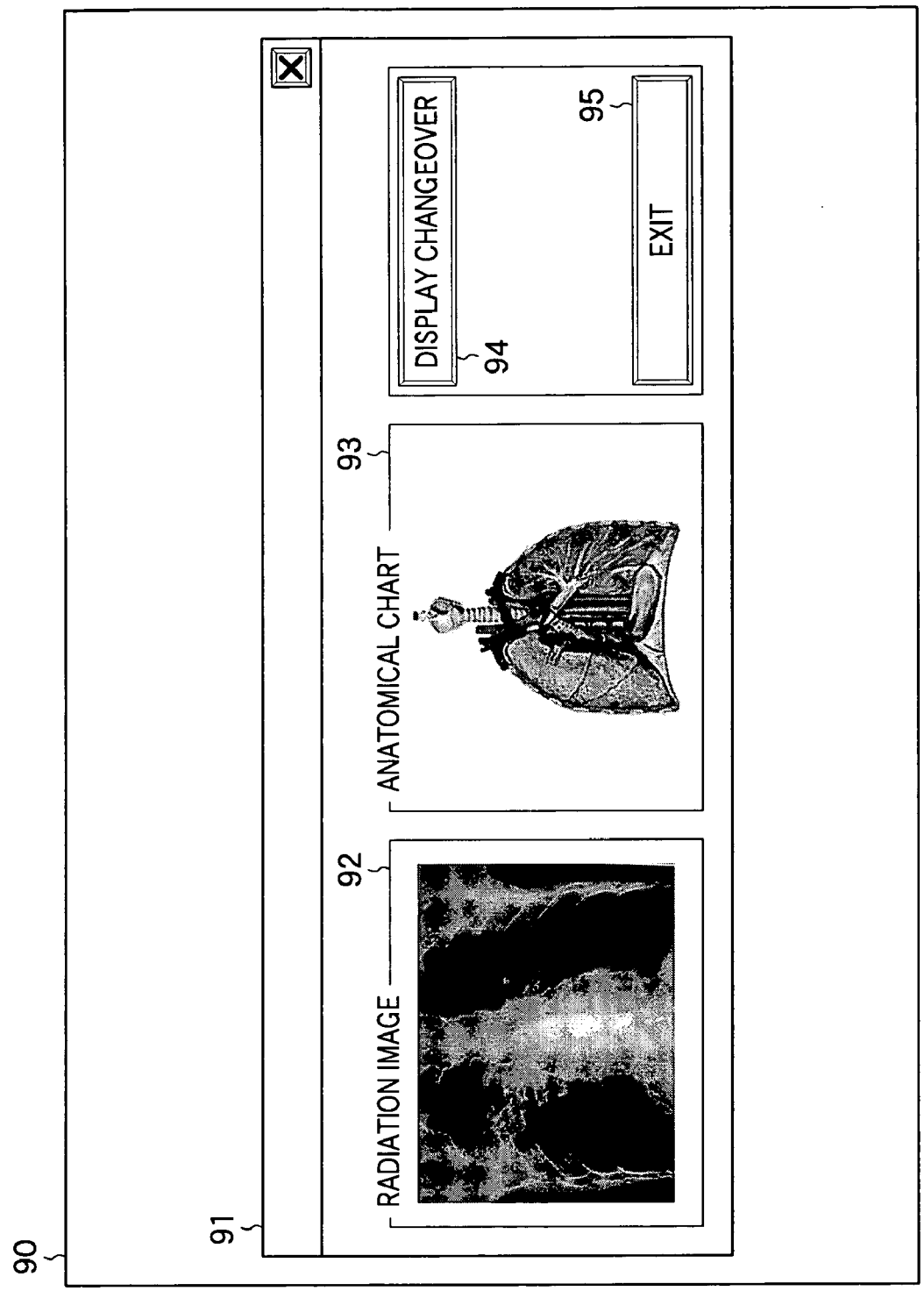
FIG. 8 shows a parallel display screen in which a radiation image and an anatomical chart are displayed side by side.

FIG. 8 shows a parallel display screen in which a radiation image and an anatomical chart are displayed side by side. On the parallel display screen 90, a menu 91 including a radiation image 92, an anatomical chart 93, a display changeover button 94 and an exit button 95 is displayed.

Thus, by displaying the radiation image and the anatomical chart, the doctor as the operator can use the anatomical chart as an object of comparison when the taken radiation image is unclear, or use when explaining the taken radiation image to the patient. The operator can instruct to switchover between the parallel display screen in which the radiation image and the anatomical chart are displayed side by side, and the superimposition screen in which the radiation image and the anatomical chart are superimposed and displayed.

When the radiation image and the anatomical chart are superimposed and displayed, the image processing unit 121b detects the overlapping of the radiation image and the anatomical chart, and obtains pixel values in the respective pixels in the overlapping part based on the alpha channel information associated with the anatomical chart data as the following equation.

(pixel value of superimposed image data) =

$(1 - \alpha) \times$ (pixel value of examination image data) +

$\alpha \times$ (pixel value of anatomical chart data)

Here, $\alpha$ is a value equal to or more than "0" and equal to or less than "1" representing the degree of transparency of the anatomical chart. The value of the alpha channel of the displayed superimposed image can be changed using the input unit 61.

In the above embodiment, the information requesting unit 121e transmits the examination attribution information by including the information in the information request signal, however, the client terminal 12 may collect data, which represents a name of sick and is obtained by this diagnosis and contained in data of electronic medical chart or the like and recorded in another terminal, in response to the instruction to download the anatomical chart, the information requesting unit 121e may transmit the data representing the name of sick by including the data in the information request signal, and the database server 24 may read out the anatomical chart filename based on the data representing the name of sick and retrieve anatomical chart data.

Further, the client terminal 12 may collect the data, which represents the name of sick and is obtained by past diagnosis and contained in data of an electronic medical chart or the like and recorded in another terminal, in response to the reception completion of a patient who has been diagnosed in the past, the information requesting unit 121e may transmit the data representing the name of sick by including the data in the information request signal, and the database server 24 may read out the anatomical chart filename based on the data representing the name of sick and retrieve the anatomical chart data.

Or, the transmission control unit 73d of the database server 24 may transmit the read anatomical chart filename together with the retrieved anatomical chart data or the like to the client terminal 12, the client terminal 12 has stored information such as anatomical chart filenames as history information of anatomical charts used in the past for the respective patients, the information requesting unit 121e of the client terminal 12, in response to the reception completion of a patient who has been diagnosed in the past, transmits an anatomical chart filename most recently or most frequently used in the history information of anatomical charts used in the past for the patient by including the filename in the information request signal, and the database server 24 may retrieve anatomical chart data based on the anatomical chart filename.

Thus, in the case where the anatomical chart data is downloaded based on the name of sick obtained in the past diagnosis and the history of anatomical charts used in the past, when a patient who has been diagnosed in the past visits the hospital again and the reception is completed, the anatomical chart data can be downloaded prior to the examination, and thereby, the anatomical chart can be displayed immediately after the examination.

The invention claimed is:

1. A diagnostic support system formed by connecting a client terminal provided in a medical facility and a database server provided in a data center via a network, said system comprising:
   a client terminal for transmitting image data, which represents a medical image obtained by imaging intended for diagnosis, and information on an examination utilizing the medical image to said database server, retransmitting the information on the examination utilizing the medical image to said database server when requesting anatomical chart data representing a desired anatomical chart, and displaying an image including the anatomical chart based on the anatomical chart data received from said database server; and
   a database server for recording the image data and the information on the examination, which are received from said client terminal, in a first recording medium, and retrieving corresponding anatomical chart data from a second recording medium, in which plural kinds of anatomical chart data are recorded, based on the received information on the examination to transmit the retrieved anatomical chart data to said client terminal when anatomical chart data is requested,
   wherein said second recording medium stores a table for associating (1) plural kinds of the name of an illness or a part to be examined, (2) anatomical chart filenames of data files, in which plural kinds of the anatomical chart data are stored respectively, and (3) alpha channel information, which represents degree of transparency when the anatomical chart is displayed by being superimposed on the medical image, together with an anatomical chart filename,
   said database server being operative to read out the alpha channel information together with the anatomical chart filename from said table, and transmit the alpha channel information together with the anatomical chart data retrieved based on the anatomical chart filename, to the client terminal.

2. The diagnostic support system according to claim 1, wherein said information on the examination includes at least one of an imaging menu representing a part to be imaged and an imaging method, a part to be examined and an image feature.

3. The diagnostic support system according to claim 2, wherein:
   said database server reads out an anatomical chart filename from said table based on the imaging menu or the part to be examined included in the information on the examination received from said client terminal, and retrieves the anatomical chart data based on the read anatomical chart filename.

4. The diagnostic support system according to claim 1, wherein:
   said client terminal superimposes and displays the medical image and the anatomical chart image based on the image data, the anatomical chart data and the alpha channel information.

5. A diagnostic support system formed by connecting a client terminal provided in a medical facility and a database server provided in a data center via a network, said system comprising:
   a client terminal for transmitting image data, which represents a medical image obtained by imaging intended for diagnosis with respect to a patient, and information on an examination utilizing the medical image to said database server, collecting data, which represents a name of an illness of the patient and is obtained by this diagnosis and recorded in another terminal, to transmit the data to said database server when requesting anatomical chart data representing a desired anatomical chart, and displaying an image including the anatomical chart based on the anatomical chart data received from said database server; and
   a database server for recording the image data and the information on the examination, which are received from said client terminal, in a first recording medium, retrieving corresponding anatomical chart data from a second recording medium, in which plural kinds of anatomical chart data are recorded, based on the received data representing the name of an illness to transmit the retrieved anatomical chart data to said client terminal when anatomical chart data is requested,
   wherein said second recording medium stores a table for associating (1) plural kinds of the name of an illness or a part to be examined, (2) anatomical chart filenames of data files, in which plural kinds of the anatomical chart data are stored respectively, and (3) alpha channel information, which represents degree of transparency when the anatomical chart is displayed by being superimposed on the medical image, together with an anatomical chart filename,
   said database server being operative to read out the alpha channel information together with the anatomical chart filename from said table, and transmit the alpha channel information together with the anatomical chart data retrieved based on the anatomical chart filename, to the client terminal.

6. The diagnostic support system according to claim 5, wherein:
   said database server reads out an anatomical chart filename from said table based on the data representing the name of an illness and received from said client terminal, and retrieves the anatomical chart data based on the read anatomical chart filename.

7. The diagnostic support system according to claim 5, wherein said data representing the name of an illness is included in electronic medical sheet data.

8. A diagnostic support system formed by connecting a client terminal provided in a medical facility and a database server provided in a data center via a network, said system comprising:
   a client terminal for collecting data, which represents name of an illness of a patient and is obtained by a past diagnosis and recorded in another terminal with respect to the patient who has completed reception, to transmit the data to said database server, transmitting image data, which represents a medical image obtained by imaging intended for diagnosis with respect to the patient, and information on an examination utilizing the medical image to said database server, and displaying an image including an anatomical chart based on anatomical chart data received from said database server; and
   a database server for recording the image data and the information on the examination, which are received from said client terminal, in a first recording medium, and retrieving, prior to a diagnosis, corresponding anatomical chart data from a second recording medium, in which plural kinds of anatomical chart data are recorded, based on the data representing the name of an illness and received from said client terminal to transmit the retrieved anatomical chart data to said client terminal, wherein said second recording medium stores a table for associating (1) plural kinds of the name of an illness or a part to be examined, (2) anatomical chart filenames of data files, in which plural kinds of the anatomical chart data are stored respectively, and (3) alpha channel information, which represents degree of transparency when the anatomical chart is displayed by being superimposed on the medical image, together with an anatomical chart filename, said database server being operative to read out the alpha channel information together with the anatomical chart filename from said table, and transmits the alpha channel information together with the anatomical chart data retrieved based on the anatomical chart filename, to the client terminal.

9. A diagnostic support system formed by connecting a client terminal provided in a medical facility and a database server provided in a data center via a network, said system comprising:

a client terminal for transmitting history information of anatomical charts utilized in a past with respect to a patient who has completed reception, to said database server, transmitting image data, which represents a medical image obtained by imaging intended for diagnosis with respect to the patient, and information on an examination utilizing the medical image to said database server, and displaying an image including the anatomical chart based on the anatomical chart data received from said database server; and a database server for recording the image data and the information on the examination, which are received from said client terminal, in a first recording medium, and retrieving, prior to a diagnosis, corresponding anatomical chart data from a second recording medium, in which plural kinds of anatomical chart data are recorded, based on the history information of anatomical charts received from said client terminal to transmit the retrieved anatomical chart data to said client terminal, wherein said second recording medium stores a table for associating (1) plural kinds of the name of an illness or a part to be examined, (2) anatomical chart filenames of data files, in which plural kinds of the anatomical chart data are stored respectively, and (3) alpha channel information, which represents degree of transparency when the anatomical chart is displayed by being superimposed on the medical image, together with an anatomical chart filename, said database server being operative to read out the alpha channel information together with the anatomical chart filename from said table, and transmits the alpha channel information together with the anatomical chart data retrieved based on the anatomical chart filename, to the client terminal.

10. The diagnostic support system according to claim 9, wherein:

said history information of anatomical charts utilized in the past includes an anatomical chart filename utilized most recently or most frequency; and said database server retrieves the anatomical chart data and alpha channel information based on the anatomical chart filename included in the history information of anatomical charts received from said client terminal.

11. A diagnostic support method to be used in a diagnostic support system formed by connecting a client terminal provided in a medical facility and a database server provided in a data center via a network, said method comprising the steps of:

(a) transmitting image data, which represents a medical image obtained by imaging intended for diagnosis, and information on an examination utilizing the medical image from said client terminal to said database server;

(b) recording the received image data and information on the examination in a first recording medium in said database server;

(c) retransmitting the information on the examination utilizing the medical image from said client terminal to said database server when requesting anatomical chart data representing a desired anatomical chart;

(d) retrieving corresponding anatomical chart data from a second recording medium, in which plural kinds of anatomical chart data are recorded, based on the received information on the examination in said database server when anatomical chart data is requested;

(e) transmitting the retrieved anatomical chart data from said database server to said client terminal; and (f) displaying on a display an image including the anatomical chart in said client terminal based on the anatomical chart data received from said database server, wherein said second recording medium stores a table for associating (1) plural kinds of the name of an illness, (2) anatomical chart filenames of data files, in which plural kinds of the anatomical chart data are stored respectively, and (3) alpha channel information, which represents degree of transparency when the anatomical chart is displayed by being superimposed on the medical image, together with an anatomical chart filename, and said retrieving step further comprises reading out the alpha channel information together with the anatomical chart filename from said table, and said transmitting step further comprises transmitting the alpha channel information together with the anatomical chart data retrieved based on the anatomical chart filename, to the client terminal.

12. The diagnostic support method according to claim 11, wherein said information on the examination includes at least one of an imaging menu representing a part to be imaged and an imaging method, a part to be examined and an image feature.

13. The diagnostic support method according to claim 12, wherein:

step (d) includes reading out an anatomical chart filename from said table based on the imaging menu or the part to be examined included in the information on the examination received from said client terminal, and retrieving the anatomical chart data based on the read anatomical chart filename.

14. The diagnostic support method according to claim 11, wherein:

step (b) includes reading out the alpha channel information together with the anatomical chart filename from said table;

step (c) includes transmitting the alpha channel information together with the anatomical chart data retrieved based on the anatomical chart filename; and step (f) includes superimposing and displaying the medical image and the anatomical chart image based on the image data, the anatomical chart data and the alpha channel information.

15. A diagnostic support method to be used in a diagnostic support system formed by connecting a client terminal provided in a medical facility and a database server provided in a data center via a network, said method comprising the steps of:

(a) transmitting image data, which represents a medical image obtained by imaging intended for diagnosis with respect to a patient, and information on an examination utilizing the medical image from said client terminal to said database server;

(b) collecting data, which represents a name of an illness of the patient and is obtained by this diagnosis and recorded in another terminal to transmit the data from said client terminal to said database server when requesting anatomical chart data representing a desired anatomical chart; and;

(c) recording the image data and the information on the examination, which are received from said client terminal, in a first recording medium in said database server;

(d) retrieving corresponding anatomical chart data from a second recording medium, in which plural kinds of anatomical chart data are recorded, in said database server based on the received data representing the name of an illness when anatomical chart data is requested;

(e) transmitting the retrieved anatomical chart data from said database server to said client terminal; and (f) displaying on a display an image including the anatomical chart in said client terminal based on the anatomical chart data received from said database server, wherein said second recording medium stores a table for associating (1) plural kinds of the name of an illness, (2) anatomical chart filenames of data files, in which plural kinds of the anatomical chart data are stored respectively, and (3) alpha channel information, which represents degree of transparency when the anatomical chart is displayed by being superimposed on the medical image, together with an anatomical chart filename, and said retrieving step further comprises reading out the alpha channel information together with the anatomical chart filename from said table, and said transmitting step further comprises transmitting the alpha channel information together with the anatomical chart data retrieved based on the anatomical chart filename, to the client terminal.

16. The diagnostic support method according to claim 15, wherein:

step (d) includes reading out an anatomical chart filename from said table based on the data representing the name of an illness and received from said client terminal, and retrieving the anatomical chart data based on the read anatomical chart filename.

17. The diagnostic support method according to claim 15, wherein said data representing the name of an illness is included in electronic medical sheet data.

18. A diagnostic support method to be used in a diagnostic support system formed by connecting a client terminal provided in a medical facility and a database server provided in a data center via a network, said method comprising the steps of:

(a) collecting data, which represents a name of an illness of a patient and is obtained by a past diagnosis and recorded in another terminal with respect to the patient who has completed reception, to transmit the data from said client terminal to said database server;

(b) retrieving corresponding anatomical chart data from a first recording medium, in which plural kinds of anatomical chart data are recorded, in said database server based on the data representing the name of an illness and received from said client terminal;

(c) transmitting the retrieved anatomical chart data from said database server to said client terminal;

(d) transmitting image data, which represents a medical image obtained by imaging intended for diagnosis with respect to the patient, and information on an examination utilizing the medical image from said client terminal to said database server;

(e) recording the image data and the information on the examination, which are received from said client terminal, in a second recording medium in said database server; and (f) displaying on a display an image including an anatomical chart in said client terminal based on the anatomical chart data received from said database server, wherein said second recording medium stores a table for associating (1) plural kinds of the name of an illness, (2) anatomical chart filenames of data files, in which plural kinds of the anatomical chart data are stored respectively, and (3) alpha channel information, which represents degree of transparency when the anatomical chart is displayed by being superimposed on the medical image, together with an anatomical chart filename, and said retrieving step further comprises reading out the alpha channel information together with the anatomical chart filename from said table, and said transmitting step further comprises transmitting the alpha channel information together with the anatomical chart data retrieved based on the anatomical chart filename, to the client terminal.

19. A diagnostic support method to be used in a diagnostic support system formed by connecting a client terminal provided in a medical facility and a database server provided in a data center via a network, said method comprising the steps of:

(a) transmitting history information of anatomical charts utilized in a past with respect to a patient who has completed reception, from said client terminal to said database server;

(b) retrieving corresponding anatomical chart data from a first recording medium in said database server, in which plural kinds of anatomical chart data are recorded, based on the history information of anatomical charts received from said client terminal;

(c) transmitting the retrieved anatomical chart data from said database server to said client terminal;

(d) transmitting image data, which represents a medical image obtained by imaging intended for diagnosis with respect to the patient, and information on an examination utilizing the medical image, from said client terminal to said database server;

(e) recording the image data and the information on the examination, which are received from said client terminal, in a second recording medium in said database server; and (f) displaying on a display an image including the anatomical chart in said client terminal based on the anatomical chart data received from said database server, wherein said second recording medium stores a table for associating (1) plural kinds of the name of an illness, (2) anatomical chart filenames of data files, in which plural kinds of the anatomical chart data are stored respectively, and (3) alpha channel information, which represents degree of transparency when the anatomical chart is displayed by being superimposed on the medical image, together with an anatomical chart filename, and said retrieving step further comprises reading out the alpha channel information together with the anatomical chart filename from said table, and said transmitting step further comprises transmitting the alpha channel information together with the anatomical chart data retrieved based on the anatomical chart filename, to the client terminal.

20. The diagnostic support method according to claim 19, wherein:

said history information of anatomical charts utilized in the past includes an anatomical chart filename utilized most recently or most frequency; and step (b) includes retrieving the anatomical chart data based on the anatomical chart filename included in the history information of anatomical charts received from said client terminal.

* * * * *